US008308755B2

(12) United States Patent
Cronin et al.

(10) Patent No.: US 8,308,755 B2
(45) Date of Patent: Nov. 13, 2012

(54) ELLIPTICAL RETRACTOR

(75) Inventors: Michael D. Cronin, Cincinnati, OH (US); Anthony T. Nguyen, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1235 days.

(21) Appl. No.: 11/902,662

(22) Filed: Sep. 24, 2007

(65) Prior Publication Data

US 2009/0082631 A1   Mar. 26, 2009

(51) Int. Cl.
A61B 1/32 (2006.01)
(52) U.S. Cl. ........................................................ 606/201
(58) Field of Classification Search ................ 600/114, 600/201–246
See application file for complete search history.

(56) References Cited

U.S. PATENT DOCUMENTS

| | | | | |
|---|---|---|---|---|
| 5,460,170 A * | 10/1995 | Hammerslag | | 600/201 |
| 5,906,577 A * | 5/1999 | Beane et al. | | 600/207 |
| 6,589,211 B1 * | 7/2003 | MacLeod | | 604/164.06 |
| 7,052,454 B2 * | 5/2006 | Taylor | | 600/114 |
| 7,153,261 B2 * | 12/2006 | Wenchell | | 600/208 |
| 7,540,839 B2 * | 6/2009 | Butler et al. | | 600/208 |
| 7,559,893 B2 * | 7/2009 | Bonadio et al. | | 600/208 |
| 7,650,887 B2 * | 1/2010 | Nguyen et al. | | 128/888 |
| 7,736,306 B2 * | 6/2010 | Brustad et al. | | 600/208 |
| 7,766,824 B2 * | 8/2010 | Jensen et al. | | 600/208 |
| 7,815,567 B2 * | 10/2010 | Albrecht et al. | | 600/208 |
| 2002/0068923 A1 * | 6/2002 | Caldwell et al. | | 606/1 |
| 2004/0054353 A1 | 3/2004 | Taylor et al. | | |
| 2004/0260153 A1 * | 12/2004 | Pulford et al. | | 600/208 |
| 2005/0283050 A1 * | 12/2005 | Gundlapalli et al. | | 600/208 |
| 2006/0161050 A1 * | 7/2006 | Butler et al. | | 600/208 |
| 2006/0229501 A1 * | 10/2006 | Jensen et al. | | 600/235 |
| 2007/0088204 A1 * | 4/2007 | Albrecht et al. | | 600/208 |

FOREIGN PATENT DOCUMENTS

| | | |
|---|---|---|
| AU | 977266 | 2/1968 |
| WO | WO 01/08581 | 2/2001 |

* cited by examiner

*Primary Examiner* — Kevin T Truong
*Assistant Examiner* — Christopher Beccia
(74) *Attorney, Agent, or Firm* — Welsh Flaxman & Gitler LLC

(57) ABSTRACT

A retractor for use in laparoscopic procedures includes an upper retractor ring, a lower retractor ring, and a retractor sheath extending between the upper retractor ring and the lower retractor ring to form a tubular passageway through which instruments or a medical practitioner's hands may pass during a medical procedure. The retractor sheath includes an elliptical passageway extending between lower retractor ring and the upper retractor ring.

20 Claims, 7 Drawing Sheets

Initial Incision

Incision Opening

Max. Incision Opening

ELLIPTICAL RETRACTOR

BACKGROUND OF THE INVENTION

1. Field of the Invention

The invention relates to a wound retractor. More particularly, the invention relates to an elliptically shaped wound retractor for use with laparoscopic surgery and in conjunction with a seal employed in hand assisted laparoscopic surgery.

2. Description of the Related Art

During laparoscopic procedures it is often necessary to inflate the abdominal cavity in order to increase the volume of the working space. This is accomplished through the utilization of insufflation gas which must be maintained at a pressure sufficient to elevate the abdominal wall. The pressure supplied by the insufflation gas is generally controlled by positioning a seal assembly at the access point for the laparoscopic surgery. The seal is connected to the wound in a manner substantially sealing off the abdominal cavity through the utilization of a retractor. The retractor extends between the seal assembly and the interior wall along the tissue.

In addition to sealing off the abdominal cavity, the retractor offers the tissue adjacent the wound protection from abrasion, bacteria or other contaminants. It also allows organs to be removed while minimizing the risk of damage to the organs.

Many retractor devices that are currently used in surgical procedures use a flexible cylindrical sleeve (circular cross-section) design to perform retraction. When placing into the incision opening, the cylindrical sleeve can be squeezed to fit into the opening. Once placed in the incision opening, the rigidity of the cylindrical sleeve determines how much the incision stays open against the compressive force of the incision walls. However, unless the sleeve is extremely rigid so as to maintain its circular cross-section, it will form an elliptical shape with corresponding values for little "d" (that is, the width of incision opening perpendicular to incision direction) and big "D" (that is, the width of incision opening parallel to incision direction) based on the rigidity of the sleeve. In order to achieve a circular shape, the rigidity of the sleeve can only be increased so much until it deters the placement of the sleeve into the incision opening.

Given the usefulness of such retractors, it is an ongoing endeavor to improve upon currently existing retractors.

SUMMARY OF THE INVENTION

It is, therefore, an object of the present invention to provide a retractor for use in laparoscopic procedures. The retractor includes an upper retractor ring, a lower retractor ring, and a retractor sheath extending between the upper retractor ring and the lower retractor ring to form a tubular passageway through which instruments or a medical practitioner's hands may pass during a medical procedure. The retractor sheath defines an elliptical passageway extending between the lower retractor ring and the upper retractor ring.

It is also an object of the present invention to provide a retractor wherein the upper retractor ring is rigid.

It is also another object of the present invention to provide a retractor wherein the upper retractor ring is circular in shape.

It is another object of the present invention to provide a retractor wherein the lower retractor ring is flexible.

It is a further object of the present invention to provide a retractor wherein the lower retractor ring is elliptical in shape.

It is still a further object of the present invention to provide a retractor wherein the lower retractor ring is circular in shape.

It is a further object of the present invention to provide a seal assembly with a retractor as described above.

Lastly, it is an object of the present invention to provide a retractor sheath having an elliptical passageway wherein the perimeter (P) of the elliptical passageway is expressed as a function of its small diameter (d) and its larger diameter (D) and the following formula:

$$P = \pi \cdot \sqrt{2 \cdot \left[\left(\frac{d}{2}\right)^2 + \left(\frac{D}{2}\right)^2\right]}$$

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
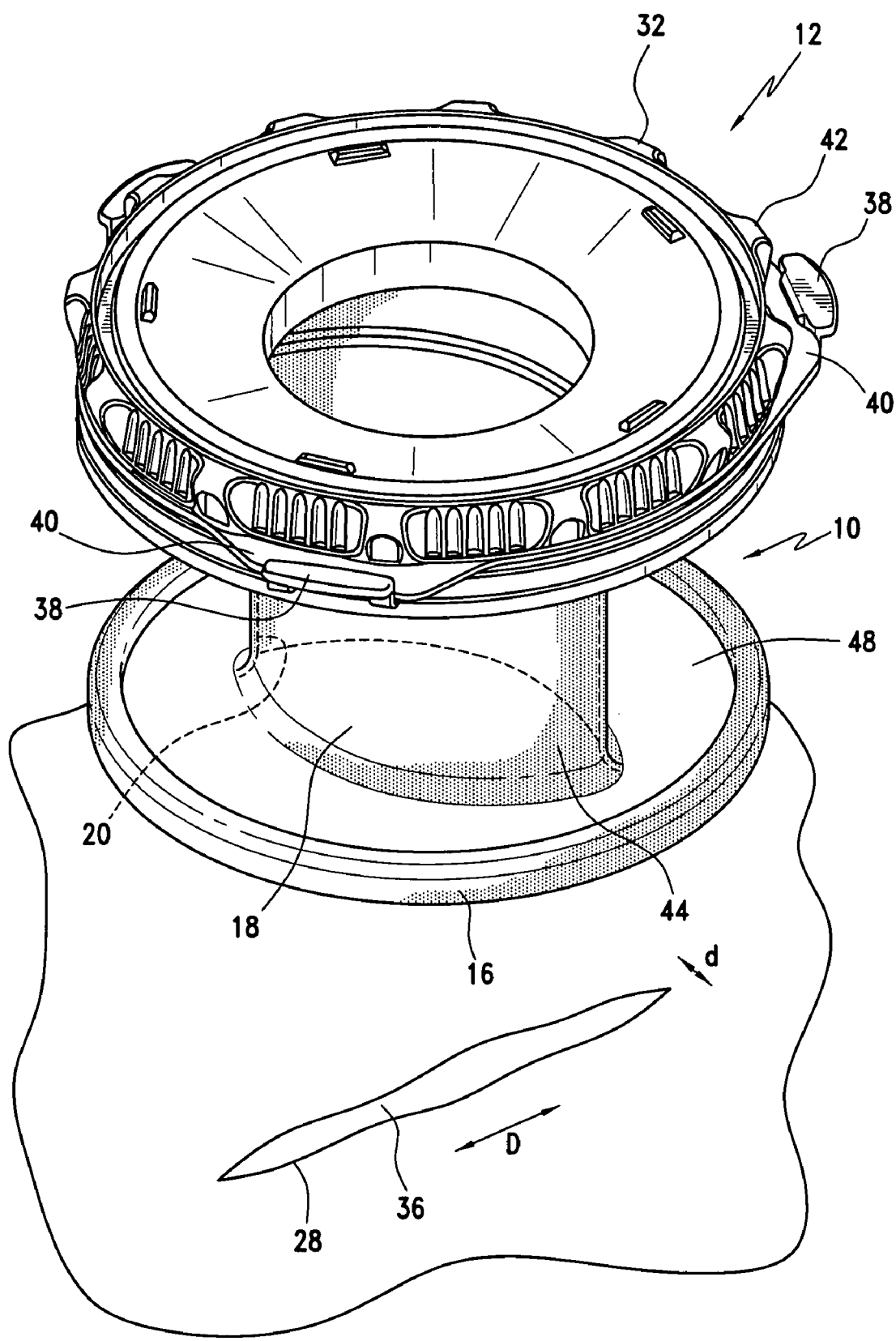
FIG. 1 is a perspective view of a laparoscopic seal assembly in accordance with the present invention prior to insertion within an incision.
Figure 2:
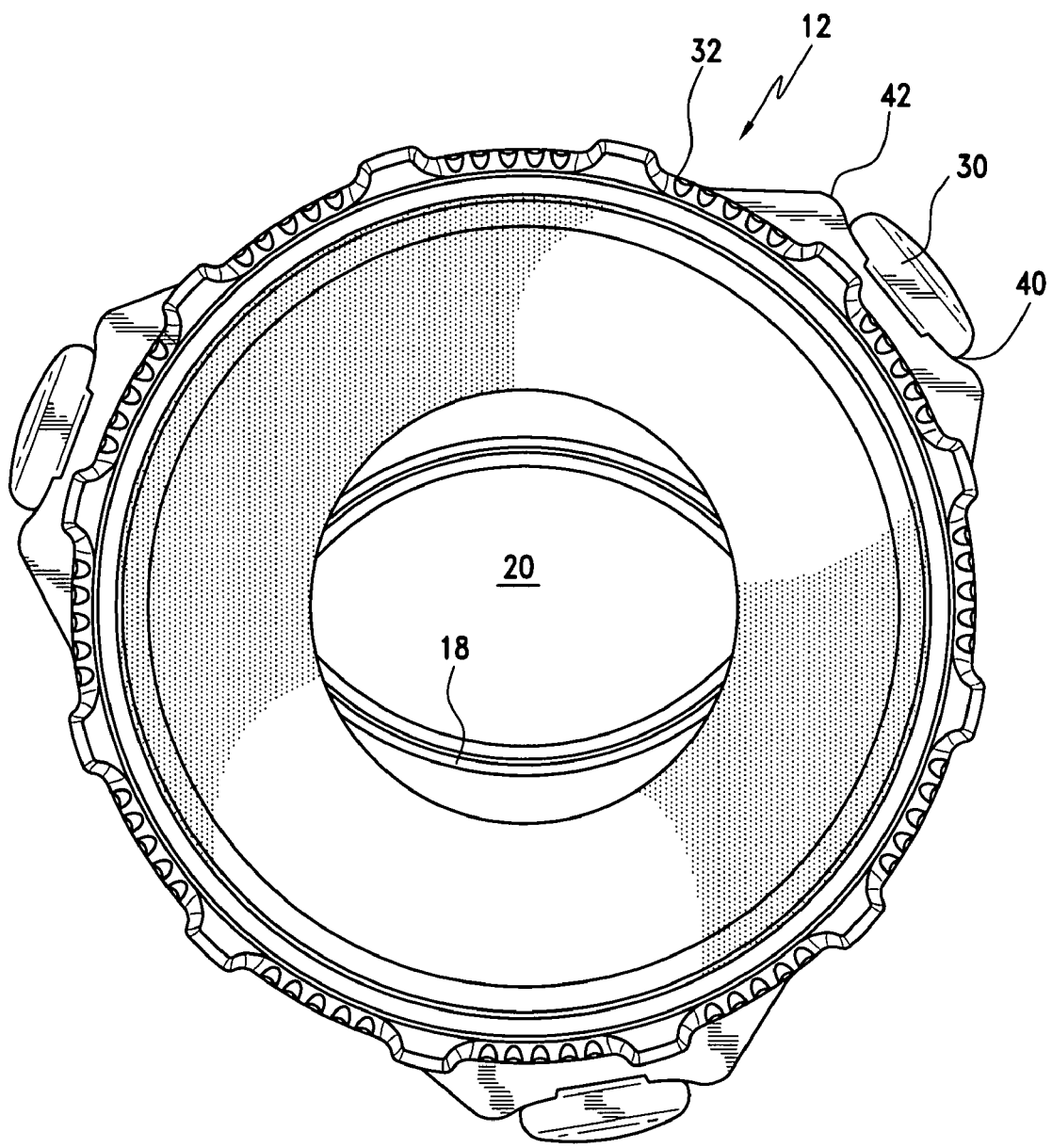
FIG. 2 is a top view of the laparoscopic seal assembly shown in FIG. 1.
Figure 3:
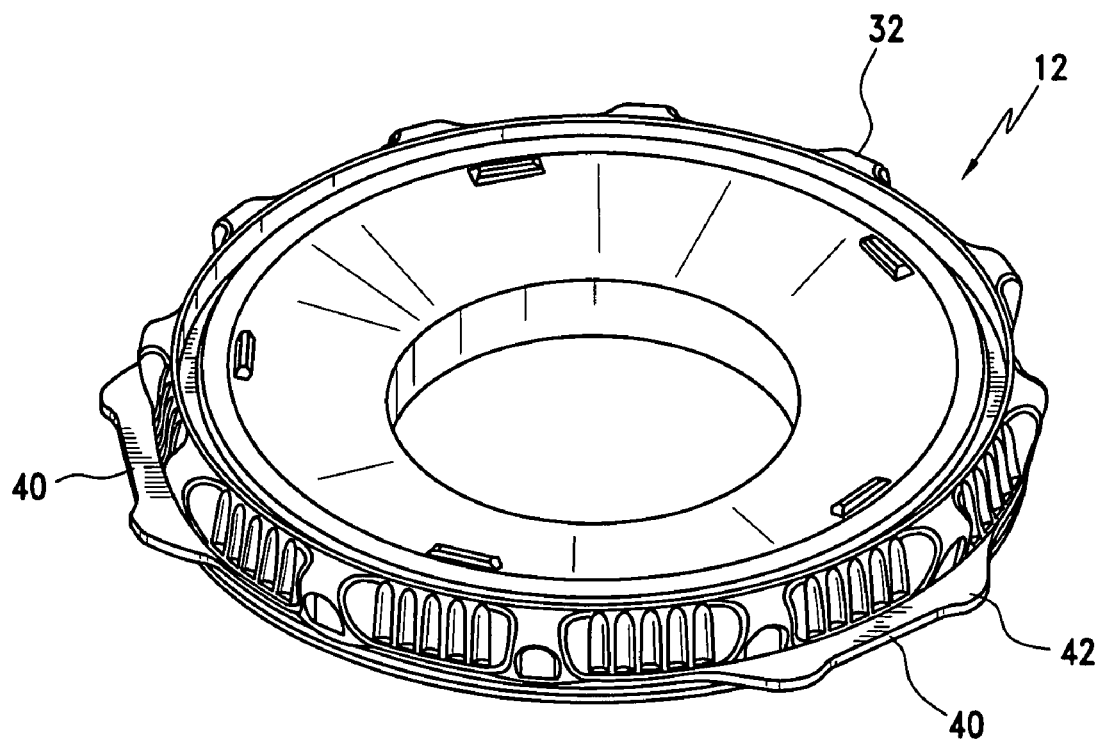
FIG. 3 is a perspective view of the seal cap in accordance with the present invention.
Figure 4:
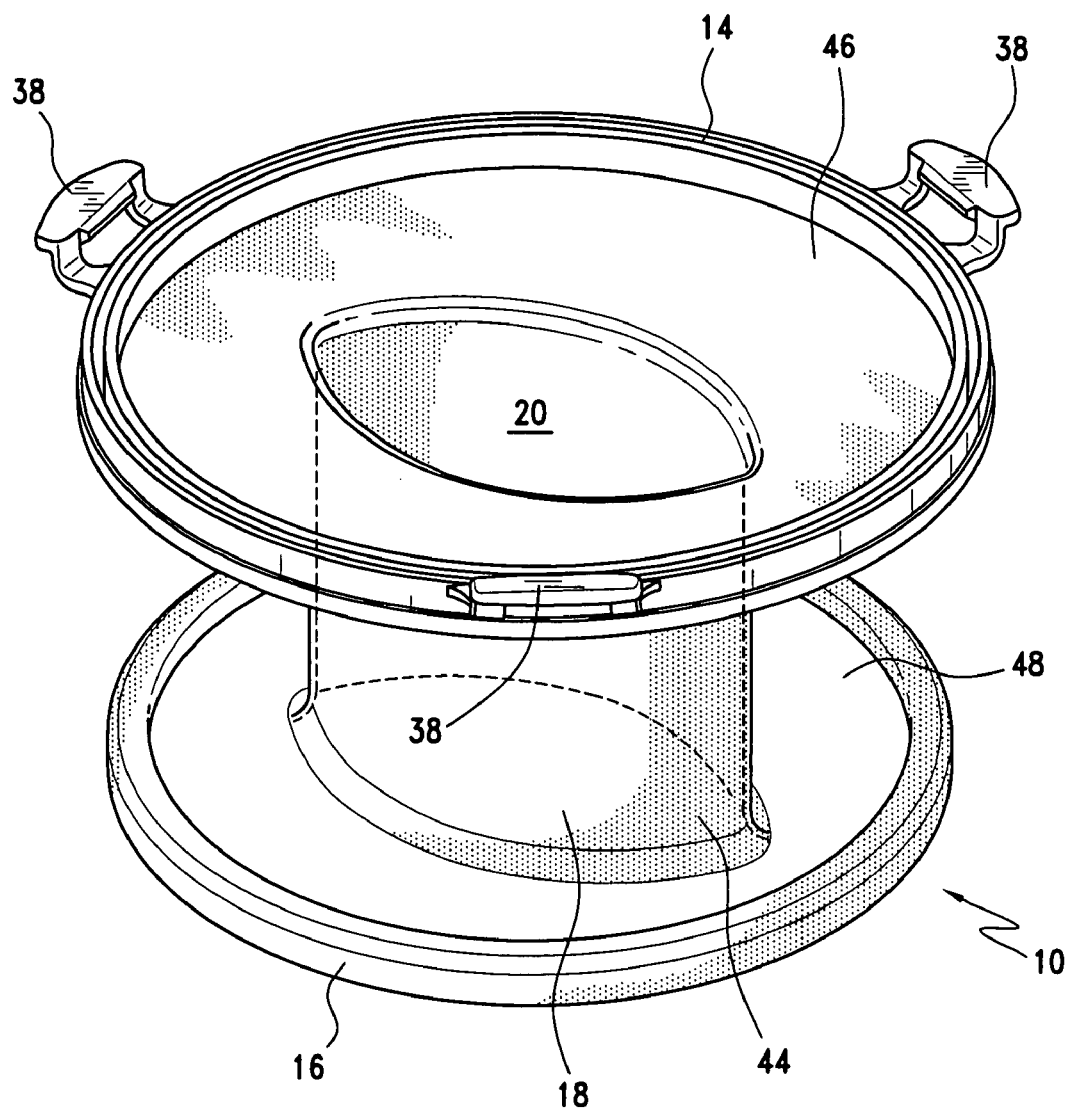
FIG. 4 is a perspective view of the retractor in accordance with the present invention.
Figure 5:
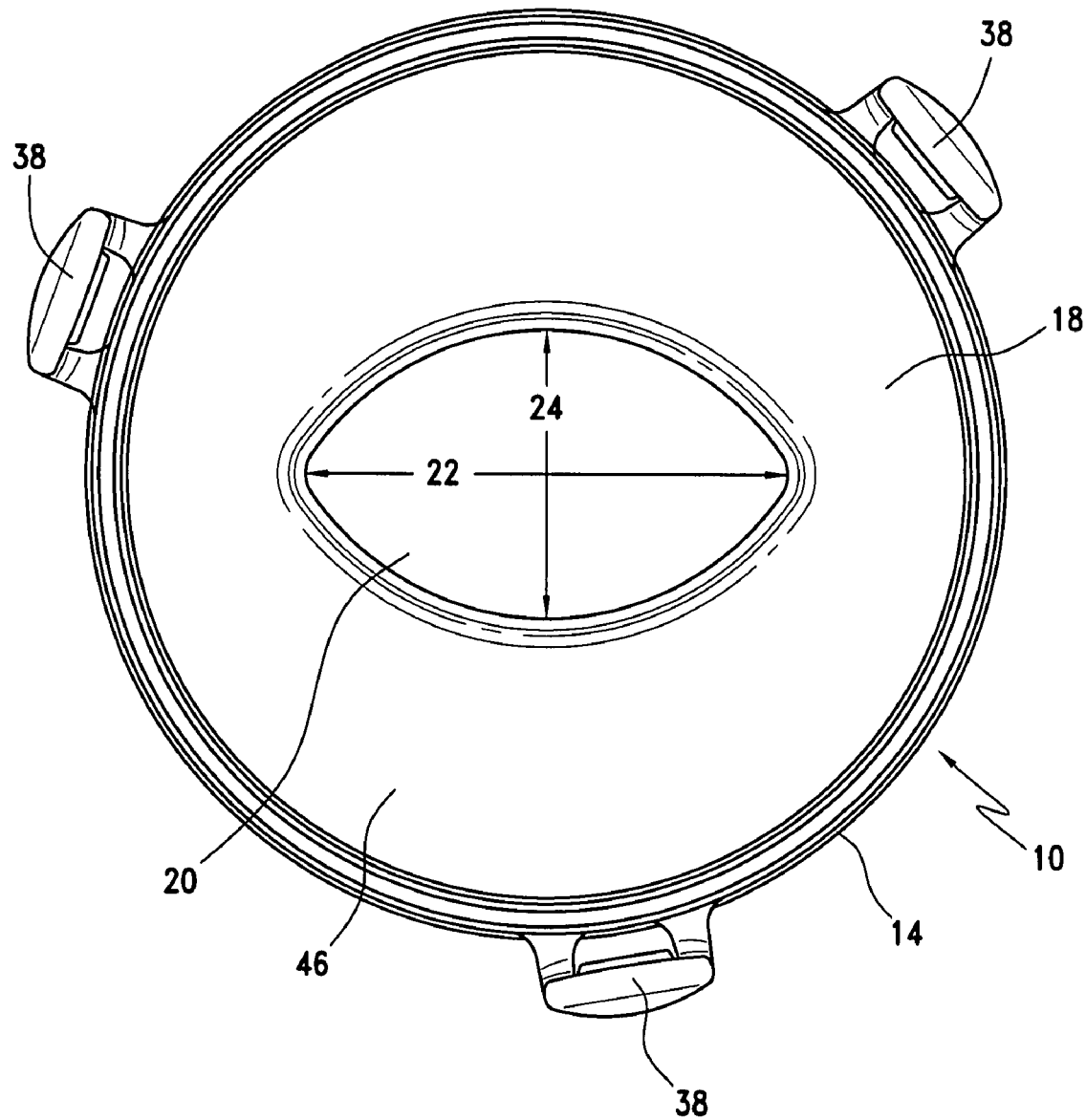
FIG. 5 is top view of retractor shown in FIG. 4.
Figure 6:
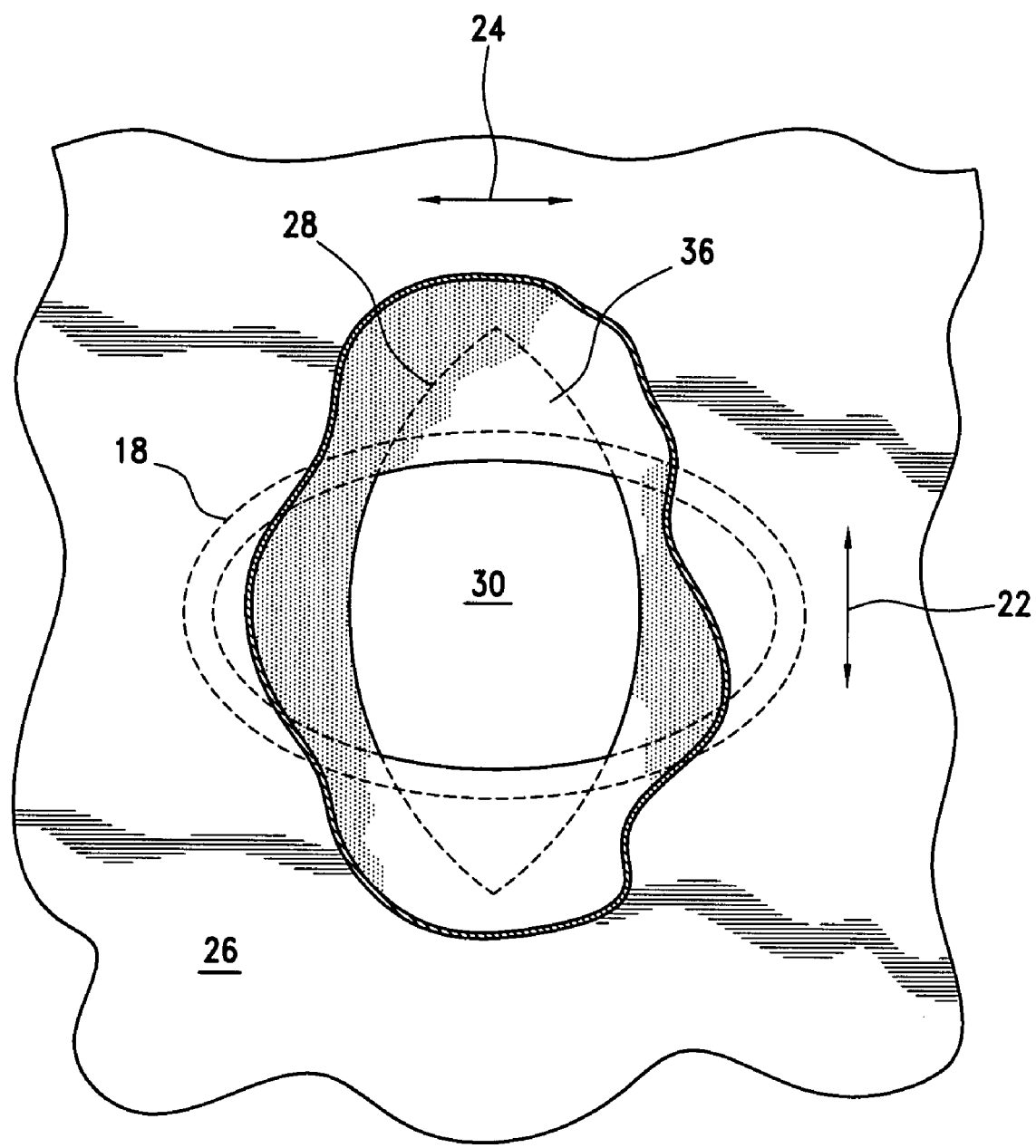
FIG. 6 is a top view of the laparoscopic seal assembly inserted and twisted within an incision.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 6, a retractor 10 in accordance with the present invention is disclosed. In accordance with the present disclosure, the retractor 10 is shown secured to a seal assembly 12 for utilization in hand assisted laparoscopic procedures. The seal assembly 12 may be similar to those disclosed in commonly owned U.S. patent application Ser. No. 11/714, 267, entitled "HAND ASSISTED LAPAROSCOPIC SEAL ASSEMBLY WITH A RATCHET MECHANISM", filed Mar. 6, 2007, which is incorporated herein by reference. Although the present retractor 10 is disclosed for use in conjunction with a seal assembly 12, those skilled in the art will appreciate the retractor 10 may be used on it own where greater access to the body cavity 30 is desired.

Briefly, the retractor 10 includes an upper retractor ring 14, a lower retractor ring 16, and a retractor sheath 18 extending between the upper retractor ring 14 and the lower retractor ring 16 to form a tubular passageway 20 through which instruments or a medical practitioner's hands may pass during a medical procedure. The retractor sheath 18 defines an elliptical passageway 20 extending between the lower retractor ring 14 and the upper retractor ring 16. In accordance with a preferred embodiment of the present invention, the retractor 10 is a fixed length retractor, although those skilled in the art will appreciate the concepts of the present invention may be applied to "roll-up" retractors without departing from the spirit of the present invention.

More particularly, the retractor 10 includes an upper retractor ring 14 and a lower retractor ring 16. The upper retractor ring 14 is a rigid ring member preferably composed of polycarbonate and the lower retractor ring 16 is a flexible ring member preferably composed of polyurethane. While polycarbonate and polyurethane are respectively disclosed as preferred materials, those skilled in the art will appreciate other materials may be employed without departing from the spirit of the present invention. For example, it is contemplated ABS (Acrylonitrile-Butadiene-Styrene), carbon-filled nylon and/or a high performance thermoplastic, such as VECTRA (a liquid crystal polyester) may be employed in the manufacture of the upper retractor ring, while polyethylene and/or thermoplastic polyurethane elastomers, such as Pellethane may be employed in the manufacture of the lower retractor ring.

The upper and lower retractor rings 14, 16 are connected by an elastic retractor sheath 18 to form a tubular passageway 20 through which instruments or a medical practitioner's hands may pass during a medical procedure. In accordance with a preferred embodiment, the retractor sheath 18 is composed of polyurethane. While polyurethane is disclosed as a preferred material, those skilled in the art will appreciate other materials such as silicon and polyethylene may be employed without departing from the spirit of the present invention. As will be discussed below in greater detail, the retractor sheath 18 is formed with a central body portion 44 having a substantially elliptical cross section when viewed within a plane that is substantially perpendicular to the longitudinal axis as the retractor 10 extends from the upper retractor ring 14 to the lower retractor ring 16.

In accordance with the preferred invention, the upper retractor ring 14 is formed in the shape of a circle, so as to maximize the space for which instruments or a medical practitioner's hands may pass. More particularly, and in accordance with a preferred embodiment of the present invention, the upper retractor ring 14 has a circular cross sectional shape when viewed within a plane that is substantially perpendicular to the longitudinal axis as the retractor 10 extends from the upper retractor ring 14 to the lower retractor ring 16.

As stated previously, the lower retractor ring 16 is flexible. In accordance with a preferred embodiment it is constructed with a circular cross sectional configuration, although it is contemplated it may be constructed with an elliptical cross sectional configuration. More particularly, the lower retractor ring 16 has an elliptical or circular cross sectional shape when viewed within a plane that is substantially perpendicular to the longitudinal axis as the retractor 10 extends from the upper retractor ring 14 to the lower retractor ring 16. However, and as those skilled in the art will certainly appreciate based upon the following disclosure, the shape of the lower retractor ring may be varied to suit specific applications without departing from the spirit of the present invention.

In order to enhance conformance of the retractor sheath 18 to the circular upper retractor ring 14 and the lower retractor ring 16, the retractor sheath 18 is shaped so as to conform to the shapes of the upper and lower retractor rings 14, 16 in the area adjacent the respective upper and lower retractor rings 14, 16. As such, the retractor sheath 18 is circular in shape adjacent the upper retractor ring 14 and either circular or elliptical adjacent the lower retractor ring 16. With this in mind, the retractor sheath 18 includes an upper transition section 46 adjacent the upper retractor ring 14 that extends from the upper retractor ring 14, which has a substantially circular cross sectional shape, to the central body portion 44, which has a substantially elliptical cross sectional shape. Similarly, the retractor sheath 18 includes a lower transition section 48 adjacent the lower retractor ring 16 that extends from the upper retractor ring 16, which has a substantially circular or elliptical cross sectional shape, to the central body portion 44, which has a substantially elliptical cross sectional shape.

As mentioned above, the retractor sheath 18 includes a central body portion 44 shaped so as to form a tube having an elliptical cross sectional shape when viewed within a plane that is substantially perpendicular to the longitudinal axis as the retractor 10 extends from the upper retractor ring 14 to the lower retractor ring 16. More particularly, the elliptical central body portion 44 of the retractor sheath 18 includes a length dimension 22 and a width dimension 24, wherein the length dimension 22 is greater than the width dimension 24. As a result, the retractor sheath 18 changes in its cross-sectional shape as it extends from the upper retractor ring 14, which is circular in shape, to the central body portion 44 of the retractor sheath 18, which is elliptical in shape, and then to the lower retractor ring 16, which is generally elliptical or circular in shape. The changes in shape are achieved through the inclusion of the upper transition section 46 and the lower transition section 48.

As is discussed below in greater detail, when the upper and lower retractor rings 14, 16 are positioned on opposite sides of the abdominal wall 26, the retractor sheath 18 is tensioned holding its elliptical shape along the central body portion 44 against the pressure being applied by the wall of the incision 28. It is the rigidity of the elliptically-shaped central body portion 44 of the retractor sheath 18 which helps to deform the incision 28 to its ideal shape for access and utilization in conjunction with a seal assembly 12 as discussed above.

More particularly, as a result of the elliptically shaped central body portion 44 of the retractor sheath 18, when the lower retractor ring 16 is positioned within the incision 28 with the length dimension 22 of the central body portion 44 of the retractor sheath 18 at 90 degrees relative to the long dimension of the incision 28, and the incision 28 is expanded to its maximum shape, the stability of the retractor 10 within the wound is maximized to prevent and/or reduce spinning of the retractor 10 within the incision 28.

Figure 7:
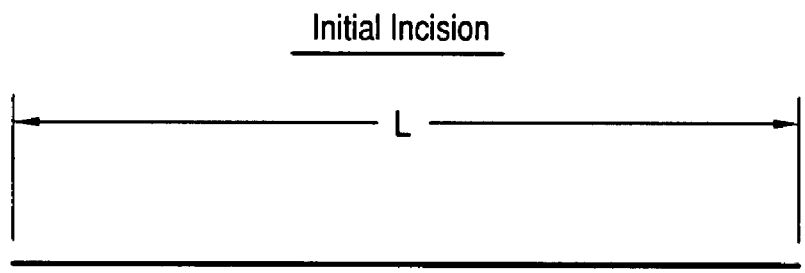
FIGS. 7, 8 and 9 are schematics showing the potential shapes for an incision.
Figure 8:
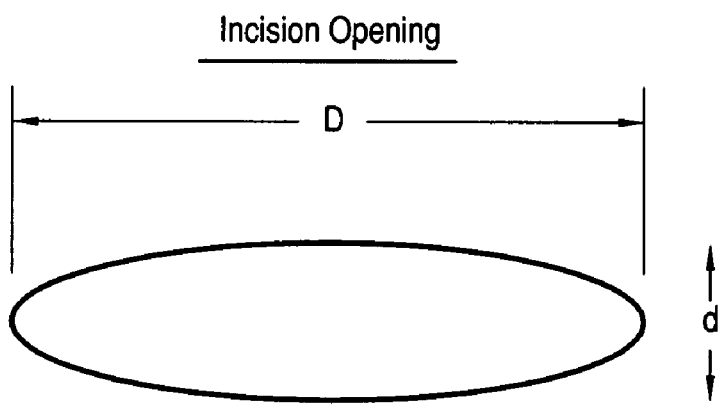
Figure 9:
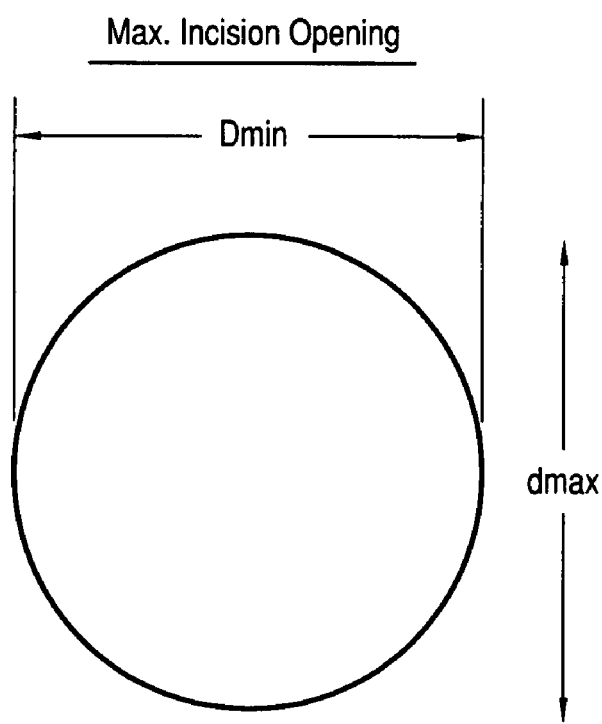

In accordance with a preferred embodiment, and with reference to FIGS. 7, 8 and 9, the oval of the central body portion 44 of the retractor sheath 18 is constructed with the following in mind:

where,
L=initial incision length
d=width of incision opening perpendicular to incision direction
D=width of incision opening parallel to incision direction
P=perimeter of incision opening Retraction performance is generally defined as the shape of the incision opening 36 that the retractor 10 can form. When the incision opening 36 is retracted, it generally forms the shape of an ellipse. The ellipse is defined by two width dimensions (or a width and length dimension depending upon one's perspective), that is, little "d" (which is dimension of the incision perpendicular to the incision direction) and big "D" (which is the dimension of the incision parallel to the incision direction). The perimeter of an ellipse can be expressed as a function of "d" and "D".

$$P = \pi \cdot \sqrt{2 \cdot \left[\left(\frac{d}{2}\right)^2 + \left(\frac{D}{2}\right)^2\right]} \quad \text{Eqn. 1}$$

The initial incision 28 length determines the size of the ellipse that can be defined by the incision 28 since it establishes the perimeter of the ellipse. The perimeter of the ellipse is substantially equal to twice the initial incision length. The incision length can, therefore, be used to establish the relationship between little "d" and big "D".

$$P = \pi \cdot \sqrt{2 \cdot \left[\left(\frac{d}{2}\right)^2 + \left(\frac{D}{2}\right)^2\right]} = 2 \cdot L \quad \text{Eqn. 2}$$

$$P^2 = \pi^2 \cdot \left(2 \cdot \left[\left(\frac{d}{2}\right)^2 + \left(\frac{D}{2}\right)^2\right]\right)$$

$$\frac{P^2}{\pi^2} = 2 \cdot \left[\left(\frac{d}{2}\right)^2 + \left(\frac{D}{2}\right)^2\right]$$

$$\frac{P^2}{2 \cdot \pi^2} = \frac{d^2}{4} + \frac{D^2}{4}$$

$$\frac{D^2}{4} = \frac{P^2}{2 \cdot \pi^2} - \frac{d^2}{4}$$

$$D = \sqrt{\frac{2 \cdot P^2}{\pi^2} - d^2}$$

$$D = \sqrt{\frac{8 \cdot L^2}{\pi^2} - d^2}$$

$$d = \sqrt{\frac{2 \cdot P^2}{\pi^2} - D^2}$$

$$d = \sqrt{\frac{8 \cdot L^2}{\pi^2} - D^2}$$

When little "d" reaches its maximum value ("dmax"), it equals big "D" at its minimum value ("Dmin"), and the equation for the perimeter of the ellipse becomes the equation for the perimeter (circumference) of a circle.

$$P = \pi \cdot \sqrt{2 \cdot \left[\left(\frac{d\max}{2}\right)^2 + \left(\frac{D\min}{2}\right)^2\right]} \quad \text{Eqn. 3}$$

$$= \pi \cdot \sqrt{2 \cdot \left[\left(\frac{d\max}{2}\right)^2 + \left(\frac{d\max}{2}\right)^2\right]}$$

$$P = \pi \cdot \sqrt{2 \cdot \left(\frac{d\max^2}{2}\right)} = \pi \cdot d\max = 2 \cdot L$$

$$d\max = \frac{2 \cdot L}{\pi} = D\min$$

In accordance with the present invention, the performance of the retractor 10 is rated based upon the size of the incision opening. Retractor 10 performance is rated best when the shape of the incision opening approaches the shape of a circle; that is when "d" is approximately the same as "D". With this in mind, the present retractor 10 is designed to create a retracted incision opening whose dimensions little "d" and big "D" will converge to equal each other (maximum little "d" equals minimum big "D").

The present retractor 10 achieves the goal of stretching the incision 28 into a substantially circular configuration by providing a retractor 10 exhibiting an elliptical cross-section designed to stretch the incision 28 into a shape approaching a circle while similarly deforming to approach the shape of a circle when compressed under the pressure of incision walls. The elliptical cross-section of the retractor sheath 18 therefore has length and width dimensions which are substantially different. When placed into the incision opening 36 with the length dimension 22 of the retractor sheath 18 oriented perpendicular to the incision direction and the width dimension 24 of the retractor sheath 18 oriented along the incision direction, the compression of the retractor sheath 18 by the walls of the incision 28 will cause the length dimension 22 of the retractor sheath 18 to decrease and the width dimension 24 of the retractor sheath 18 to increase (see FIG. 6). As those skilled in the art will certainly appreciate, the dimensions of the retractor sheath 18 and the rigidity of the retractor sheath 18 can then be optimized so that little "d" and big "D" of the incision 28 will converge to equal each other and, therefore, form an incision opening with a circular shape.

As defined previously, the incision length establishes the perimeter of the incision opening 36. With a known perimeter, the relationship for little "d" and big "D" can also be established. The limits for little "d" and big "D" will, therefore, depend on the typical incision length sizes. From Eqn. 3, the maximum value for little "d" ("dmax") and the minimum value for big "D" ("Dmin") can be calculated from the incision length. The following table lists calculated values for "dmax" and "Dmin" based on some typical incision lengths.

| Incision Length (cm) | Incision Perimeter (cm) | "Dmin" or "dmax" (cm) |
|---|---|---|
| 5.0 | 10.0 | 3.2 |
| 5.5 | 11.0 | 3.5 |
| 6.0 | 12.0 | 3.8 |
| 6.5 | 13.0 | 4.1 |
| 7.0 | 14.0 | 4.5 |
| 7.5 | 15.0 | 4.8 |
| 8.0 | 16.0 | 5.1 |
| 8.5 | 17.0 | 5.4 |
| 9.0 | 18.0 | 5.7 |

The range of little "d" can be between zero and "dmax" while the range of big "D" can be between "Dmin" and the incision length. The initial starting dimensions for the elliptical retractor 10 will depend on the target value for the incision perimeter (retractor 10 perimeter) and a starting value for either little "d" or big "D." An example of designing an elliptical retractor 10 device is shown below.

In order to accommodate a varying range of incision lengths, a possible retractor design could target the nominal incision length, which in the above table is 7.0 cm and results in a perimeter of 14.0 cm. Another design factor that needs to be considered is the value for big "D" such that placement of the retractor 10 in the incision opening is not hindered. To help facilitate placement of the retractor 10 for small incision sizes, a possible value for big "D" could be 5.0 cm, which represents the smallest incision length in the above table. Using Eqn. 2, the little "d" can be calculated. The following calculations shows an example of an elliptical retractor design based on a retractor perimeter of 14.0 cm and a big "D" of 5.0 cm.

$$d = \sqrt{\frac{2 \cdot P^2}{\pi^2} - D^2} = \sqrt{\frac{2 \cdot (14)^2}{\pi^2} - (5)^2}$$

$$d = 3.8$$

In practice, the retractor 10 and the remainder of a seal assembly 12 are secured to the abdominal wall 26 of an individual patient by first creating an incision 28 and positioning the retractor 10 above the incision 28. Thereafter, the lower retractor ring 16 of the retractor 10 is inserted into the body cavity 30 with the abdominal wall 26 between the upper retractor ring 14 and the lower retractor ring 16. The tension between the upper retractor ring 14 and the lower retractor ring 16 as they extend between the external and internal portion of the incision 28 creates substantial rigidity in the central body portion 44 of the retractor sheath 18 allowing for stretching of the incision 28 in a manner optimizing retraction thereof in a manner discussed herein in greater detail. A seal cap 32 of the seal assembly 12 is then connected to the upper retractor ring 14 of the retractor 10. In accordance with a preferred embodiment of the present invention, the upper retractor ring 14 is provided with a series of resilient latch members 38 which are shaped and dimensioned to engage recesses 40 in the sidewall 42 of the seal cap 32 for securing the retractor 18 to the seal cap 32. As those skilled in the art will certainly appreciate, various mechanisms are available for securing a retractor to a seal cap. Examples of such coupling structures are disclosed in commonly owned U.S. patent application Ser. No. 11/730,922, entitled "HAND ASSISTED LAPAROSCOPIC SEAL ASSEMBLY WITH DETACHABLE ATTACHMENT RING", filed Apr. 4, 2007, which is incorporated herein by reference.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision 28. For example, if the surgeon's glove size is 7, a 6.5 to 7.0 cm incision 28 is usually appropriate. Thereafter, an incision 28 is made along the marked incision line. The incision size is thereafter verified by inserting the surgeon's hand into the abdomen prior to installing the retractor 10 and the remainder of the seal assembly 12. If the incision is too small, the incision is extended on each end as required to maintain the central position of the incision relative to the placement of the present seal assembly 12. Thereafter, the lower retractor ring 16 of the retractor 10 is inserted through the incision 28. Using one's fingers, the lower retractor ring 16 of the retractor 10 is seated evenly under the peritoneum and the area is swept to ensure the retractor 10 is not lying between tissue layers. In view of the shape of the retractor sheath 18, and, in particular, the central body portion 44, minimal resistance to insertion is achieved by orienting the retractor 10 so the length dimension 22 is oriented substantially parallel to the length of the incision 28. The upper retractor ring 14 and the lower retractor ring 16 are positioned on opposite sides of the abdominal wall 26. The tension between the upper retractor ring 14 and the lower retractor ring 16 as they extend between the external and internal portion of the incision 28 creates substantial rigidity in the retractor sheath 18 allowing for stretching of the incision 28 in a manner optimizing retraction thereof in a manner discussed herein in greater detail. The retractor 10 is then rotated 90 degrees so the length dimension 22 of the central body portion 44 of the retractor sheath 18 is oriented perpendicular to the length of the incision 28. This orientation orients the central body portion 44 of the retractor sheath 18 such that it expands the little "d" dimension of the incision 28 so as to expand the wound to its maximum shape and the stability of the retractor 10 is maximized to prevent or reduce spinning of the retractor 10 within the incision 28 (see FIG. 6).

Thereafter, the seal cap 32 is attached to the upper retractor ring 14 of the retractor 10 and adjustments are made to ensure the seal assembly 12 is secured with the patient's abdomen maintaining pneumo.

As those skilled in the art will certainly appreciate, the concepts underlying the present retractor may be applied to fixed length or adjustable length retractors. In either case, the retractor must fit the abdominal wall thickness to maintain stability and pneumo.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A retractor for use in laparoscopic procedures, comprising:
    an upper retractor ring;
    a lower retractor ring; and
    a retractor sheath connecting the upper retractor ring and the lower retractor ring to form a tubular passageway through which instruments or a medical practitioner's hands may pass during a medical procedure;
    wherein the retractor sheath includes a tubular central body portion having a substantially elliptical cross section when viewed within a plane that is substantially perpendicular to a longitudinal axis as the retractor extends from the upper retractor ring to the lower retractor ring so as to define an elliptical passageway extending between the lower retractor ring and the upper retractor ring.

2. The retractor according to claim 1, wherein the upper retractor ring is rigid.

3. The retractor according to claim 2, wherein the upper retractor ring is circular in shape, and the retractor sheath includes an upper transition section positioned adjacent the upper retractor ring, the upper transition section extends from the upper retractor ring to the central body portion.

4. The retractor according to claim 1, wherein the upper retractor ring is circular in shape, and the retractor sheath includes an upper transition section positioned adjacent the upper retractor ring, the upper transition section extends from the upper retractor ring to the central body portion.

5. The retractor according to claim 1, wherein the lower retractor ring is flexible.

6. The retractor according to claim 1, wherein the lower retractor ring is elliptical in shape.

7. The retractor according to claim 1, wherein the lower retractor ring is circular in shape, and the retractor sheath includes an lower transition section positioned adjacent the upper retractor ring, the lower transition section extends from the lower retractor ring to the central body portion.

8. The retractor according to claim 5, wherein the lower retractor ring is elliptical in shape.

9. The retractor according to claim 5, wherein the lower retractor ring is circular in shape, and the retractor sheath includes an lower transition section positioned adjacent the upper retractor ring, the lower transition section extends from the lower retractor ring to the central body portion.

10. The retractor according to claim 1, wherein the perimeter (P) of the elliptical passageway is expressed as a function of its small diameter (d) and its larger diameter (D) and the following formula:

$$P = \pi \cdot \sqrt{2 \cdot \left[\left(\frac{d}{2}\right)^2 + \left(\frac{D}{2}\right)^2\right]}.$$

11. A seal assembly with retractor for use in laparoscopic procedures, comprising:
   a seal cap;
   a retractor secured to the seal cap, the retractor including:
     an upper retractor ring;
     a lower retractor ring; and
     a retractor sheath connecting the upper retractor ring and the lower retractor ring to form a tubular passageway through which instruments or a medical practitioner's hands may pass during a medical procedure;
     wherein the retractor sheath includes a tubular central body portion having a substantially elliptical cross section when viewed within a plane that is substantially perpendicular to a longitudinal axis as the retractor extends from the upper retractor ring to the lower retractor ring so as to define an elliptical passageway extending between the lower retractor ring and the upper retractor ring.

12. The seal assembly with retractor according to claim 11, wherein the upper retractor ring is rigid.

13. The seal assembly with retractor according to claim 12, wherein the upper retractor ring is circular in shape, and the retractor sheath includes an upper transition section positioned adjacent the upper retractor ring, the upper transition section extends from the upper retractor ring to the central body portion.

14. The seal assembly with retractor according to claim 11, wherein the upper retractor ring is circular in shape, and the retractor sheath includes an upper transition section positioned adjacent the upper retractor ring, the upper transition section extends from the upper retractor ring to the central body portion.

15. The seal assembly with retractor according to claim 11, wherein the lower retractor ring is flexible.

16. The seal assembly with retractor according to claim 11, wherein the lower retractor ring is elliptical in shape.

17. The seal assembly with retractor according to claim 11, wherein the lower retractor ring is circular in shape, and the retractor sheath includes an lower transition section positioned adjacent the upper retractor ring, the lower transition section extends from the lower retractor ring to the central body portion.

18. The seal assembly with retractor according to claim 15 wherein the lower retractor ring is elliptical in shape.

19. The seal assembly with retractor according to claim 15, wherein the lower retractor ring is circular in shape, and the retractor sheath includes an lower transition section positioned adjacent the upper retractor ring, the lower transition section extends from the lower retractor ring to the central body portion.

20. The seal assembly with retractor according to claim 11, wherein the perimeter (P) of the elliptical passageway is expressed as a function of its small diameter (d) and its larger diameter (D) and the following formula:

$$P = \pi \cdot \sqrt{2 \cdot \left[\left(\frac{d}{2}\right)^2 + \left(\frac{D}{2}\right)^2\right]}.$$

* * * * *